(12) United States Patent
Jackovitch

(10) Patent No.: US 7,753,866 B2
(45) Date of Patent: Jul. 13, 2010

(54) FLEXION CONTROL ANKLE JOINT WITH SPHERICAL HINGE

(76) Inventor: Timothy Jackovitch, 7521 Fieldstone Way, Monroe, GA (US) 30656

( * ) Notice: Subject to any disclaimer, the term of this patent is extended or adjusted under 35 U.S.C. 154(b) by 418 days.

(21) Appl. No.: 11/899,976

(22) Filed: Sep. 7, 2007

(65) Prior Publication Data

US 2009/0069732 A1    Mar. 12, 2009

(51) Int. Cl.
  *A61F 5/00*    (2006.01)
  *A61F 5/37*    (2006.01)
  *A61F 13/00*   (2006.01)
  *A61B 19/00*   (2006.01)
  *E05D 7/00*    (2006.01)

(52) U.S. Cl. .............. 602/27; 602/5; 602/16; 602/23; 602/28; 602/29; 128/846; 128/869; 128/882; 16/224

(58) Field of Classification Search ........ 602/5, 602/16, 23, 27, 28, 29, 65; 128/869, 882; 16/223, 224; 24/67.7
See application file for complete search history.

(56) References Cited

U.S. PATENT DOCUMENTS

| | | | |
|---|---|---|---|
| 292,800 A | 2/1884 | Furrer | |
| 3,982,278 A | 9/1976 | May | |
| 4,320,747 A | 3/1982 | Daniell, Jr. | |
| 4,499,613 A | 2/1985 | Yarrow | |
| 4,605,417 A | 8/1986 | Fleischauer | |
| 4,614,181 A | 9/1986 | Karlsson | |
| 4,728,336 A | 3/1988 | Cooper | |
| 5,112,356 A | 5/1992 | Harris et al. | |
| 5,156,630 A | 10/1992 | Rappoport et al. | |
| 5,242,379 A | 9/1993 | Harris et al. | |
| 5,244,455 A | 9/1993 | Swicegood et al. | |
| 5,443,527 A | 8/1995 | Wilson | |
| 5,482,513 A | 1/1996 | Wilson | |
| 5,542,774 A | 8/1996 | Hoy | |
| 5,545,234 A | 8/1996 | Collier, Jr. | |
| 5,611,773 A | 3/1997 | Nash et al. | |
| 5,695,526 A | 12/1997 | Wilson | |
| 5,728,175 A | 3/1998 | Rincoe | |
| 5,746,773 A | 5/1998 | Littig | |
| 5,766,264 A | 6/1998 | Lundt | |

(Continued)

OTHER PUBLICATIONS

Becker Orthopedic, Becker Orthopedic Online Catalog, pp. 224-226, printed Jul. 30, 2007.

*Primary Examiner*—Patricia M Bianco
*Assistant Examiner*—Brandon Jackson
(74) *Attorney, Agent, or Firm*—James Richards

(57) ABSTRACT

A joint hinge and a leg brace having the joint hinge that includes a spring loaded spherical joint for coupling a proximal portion and a distal portion of the joint hinge. The spherical joint includes a dome on one portion coupled to a mating cup on the other portion. A wide-headed pin, typically a shoulder screw, captivates the cup against the sphere. A spring washer may be included to provide a preloading force to mate the cup to the dome. The spherical portion may be pressed or stamped into one portion of the hinge or fabricated separately and attached. In one embodiment, the dome is fabricated of sintered bearing material and may be impregnated with lubricant. The spherical joint functions in conjunction with an adjustable flexion range limiting system that include rods that are threaded and easy to screw in and out as the patient's range of motion changes.

12 Claims, 7 Drawing Sheets

U.S. PATENT DOCUMENTS

| | | |
|---|---|---|
| 5,851,194 A | 12/1998 | Fratrick |
| 5,954,677 A | 9/1999 | Albrecht et al. |
| 5,997,493 A | 12/1999 | Young |
| 6,033,440 A | 3/2000 | Schall et al. |
| 6,231,618 B1 | 5/2001 | Schall et al. |
| D448,484 S | 9/2001 | Bradshaw |
| 6,375,632 B1 | 4/2002 | Albrecht et al. |
| 6,635,024 B2 | 10/2003 | Hatton et al. |
| D489,135 S | 4/2004 | Slautterback et al. |
| 6,752,774 B2 | 6/2004 | Townsend et al. |
| 6,824,523 B2 | 11/2004 | Carlson |
| 6,929,614 B1 | 8/2005 | Jackovitch |
| 7,364,534 B2 * | 4/2008 | Zoller et al. .................. 482/80 |
| 2004/0127825 A1 | 7/2004 | Castillo et al. |

* cited by examiner

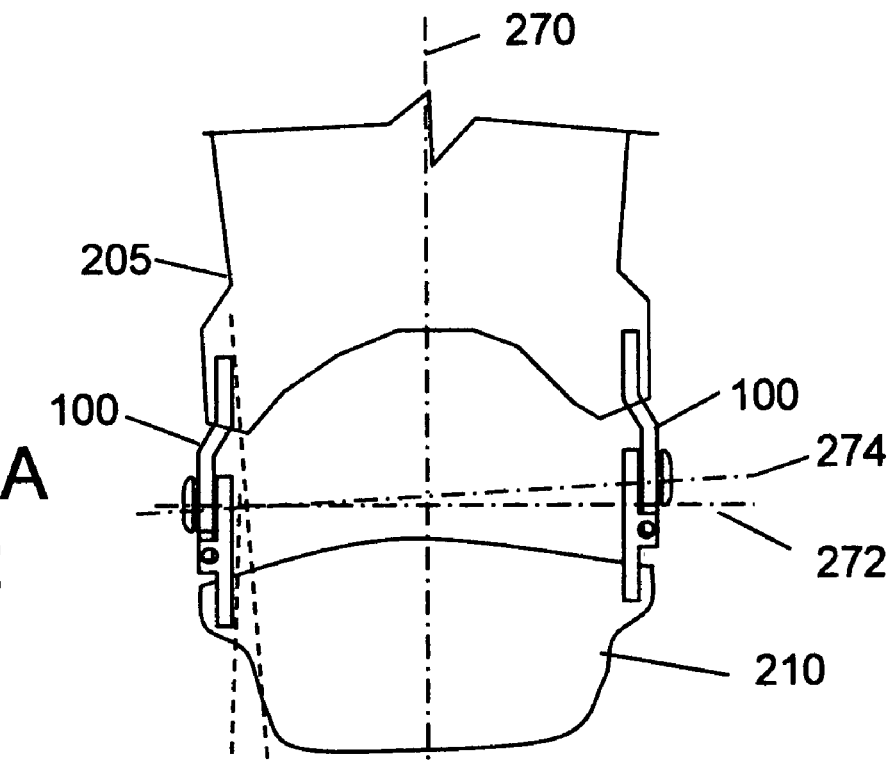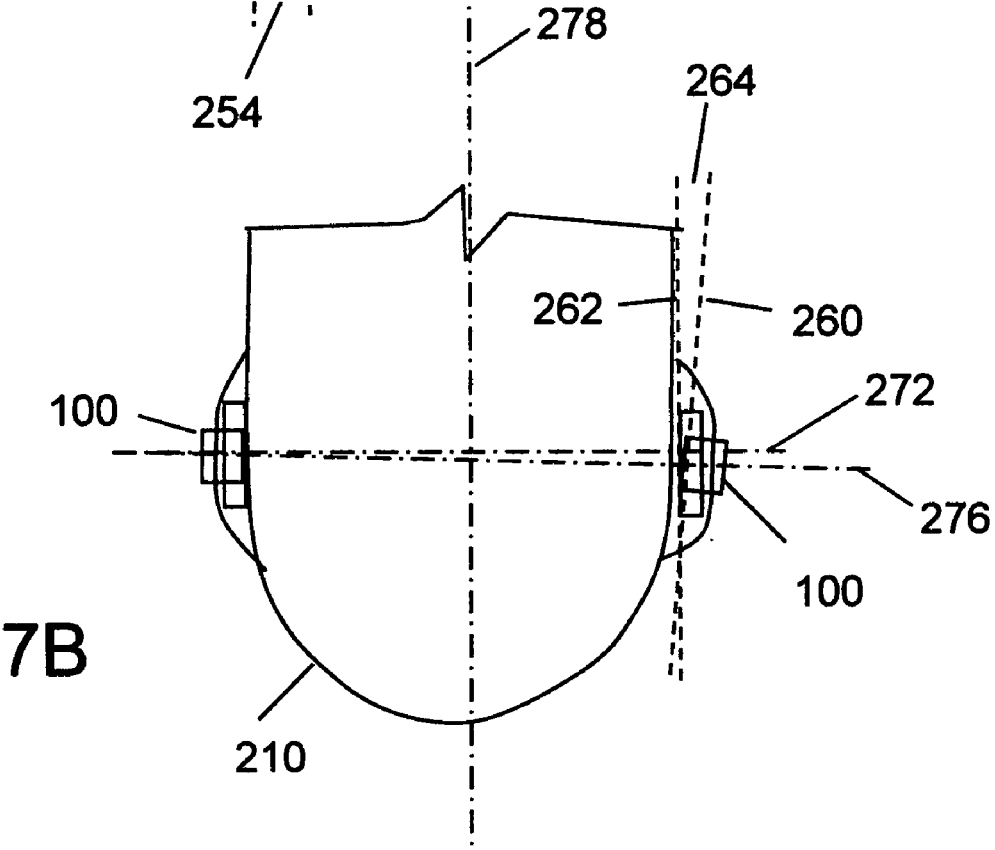

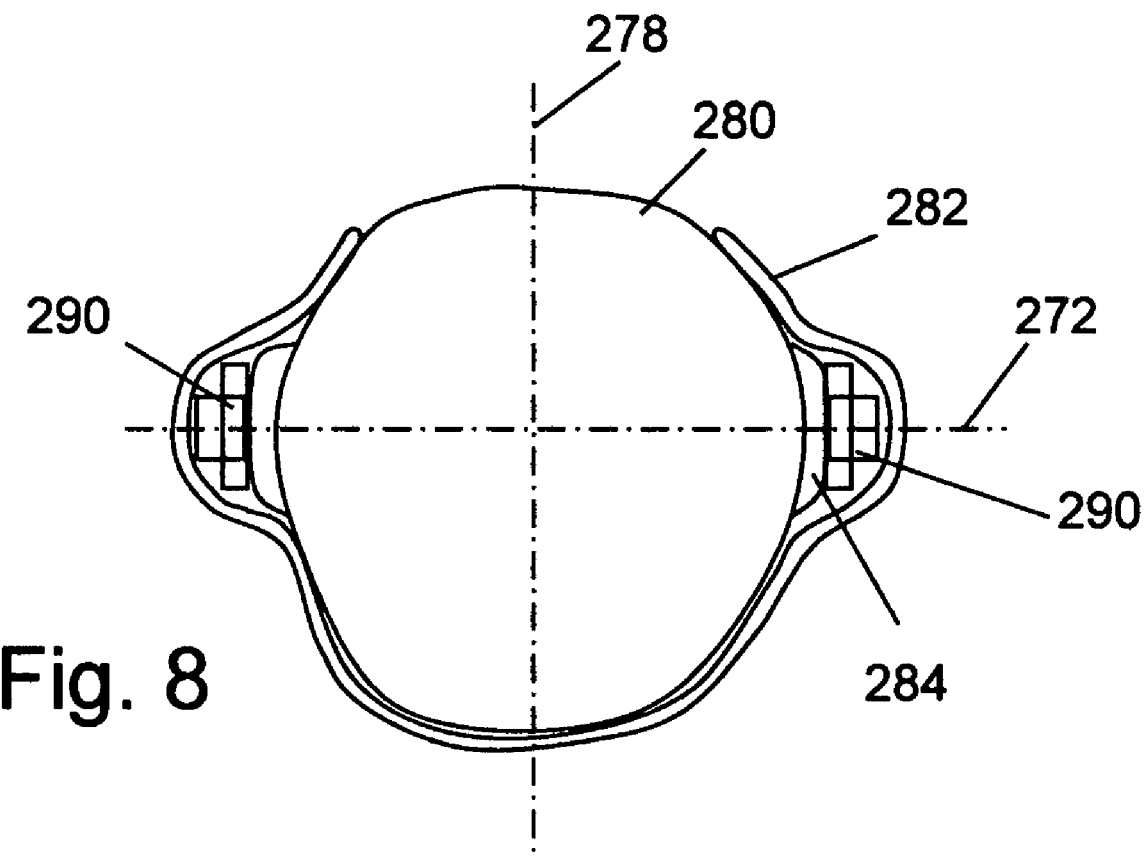
Fig. 8
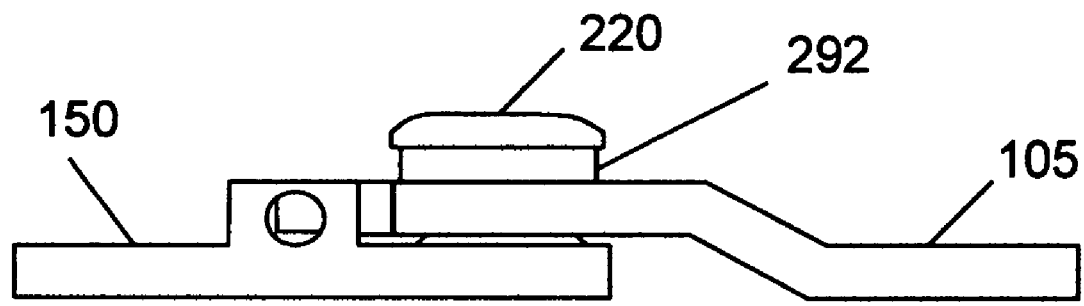
Fig. 9

FLEXION CONTROL ANKLE JOINT WITH SPHERICAL HINGE

BACKGROUND

1. Field of the Invention

The present invention relates generally to the field of orthotic devices and more particularly to ankle foot orthoses with a flexion control ankle hinge apparatus, system and method.

2. Background of the Invention

Present ankle joints for leg braces can offer control of plantar flexion and dorsiflection as shown in U.S. Pat. No. 6,929,614 issued Aug. 16, 2005 to Jackovitch, which is incorporated herein by reference. However, these and other prior art ankle joints are often difficult to install, requiring precisely parallel mounting surfaces for medial and lateral joint mechanisms. Without proper mounting the joints may be subject to greater wear, binding, and stress on the leg brace components, leading to cracks and possible failure. Achieving proper installation requires additional shimming or shaping or remaking of the leg brace components, taking extra time for the practitioner and potentially leading to extra complication and cost for the patient.

Devices that offer plantar flexion control include devices that are bulky and difficult to fit in the patient's shoe, and are difficult to adjust due to the fact that they include definite settings that can only be adjusted in increments. Other devices require separate pieces, such as range of motion keys, which must be inserted and replaced as the patient's range of motion increases or decreases. Often these devices are large and cause additional complications with smaller patients, such as pediatric patients.

Thus, there is a need for an ankle joint that can be fitted to a leg brace and automatically accommodates slight misalignment of leg brace components and non parallelism of mounting surfaces while providing for plantar flexion limits. The ankle joint should be compact in size allowing potential use with pediatric patients.

BRIEF DESCRIPTION OF THE INVENTION

Briefly, the present invention relates to a joint hinge and a leg brace having the joint hinge that includes a spring loaded spherical joint for coupling a proximal portion and a distal portion of the joint hinge. The spherical joint includes a dome on one portion coupled to a mating cup on the other portion. The spherical dome presents a spherical surface for contacting the mating cup, the spherical surface consisting of a portion of a hemisphere less than a full hemisphere. A wide headed pin, typically a shoulder screw, captivates the cup against the sphere. A spring washer may be included to provide a preloading force to mate the cup to the dome. The spherical portion may be pressed or stamped into one portion of the hinge. In one embodiment, the dome is fabricated of sintered bearing material and may be impregnated with lubricant.

The spherical joint functions in conjunction with an adjustable flexion range limiting system that include rods that are threaded and easy to screw in and out as the patient's range of motion changes. In a typical embodiment, a proximal plate rotates about the spherical joint with respect to a distal plate. The spherical joint is generally aligned with the patient's ankle axis. The range limiting system's rods screw toward and away from a portion of the proximal plate, thereby limiting the range of the proximal, and therefore, the distal plates. The proximal plate is connected to one portion of the leg brace and the distal plate is connected to the other portion of the leg brace.

One aspect of the invention features a flexion joint apparatus incorporated into a leg brace, including a proximal plate having an upper end and a lower end, a distal plate connected to the proximal plate and an anterior-posterior range limiting system, including a tongue connected to the second end of the proximal plate, and two tongue-stops connected to the distal plate at a generally perpendicular orientation, wherein each of the tongue-stops includes a threaded hole through which a threaded rod is connected to the tongue-stops in threaded engagement.

In another aspect, the apparatus further includes a conduit located on the distal plate and partially surrounding each of the threaded rods.

In yet another aspect, the apparatus includes leg brace connection points located on the proximal and distal plates, each leg brace connection point, comprising a generally circular-shaped base surrounding a hole.

In another aspect, the invention features a flexion joint apparatus, including a proximal plate having a tongue protruding from an end of the proximal plate, a distal plate having a protrusion connected generally perpendicular to each side of the distal plate, wherein the tongue of the proximal plate overlaps a portion of the distal plate and travels a path along the distal plate, each end of the path terminating in a respective one of the protrusions.

In still another aspect, the invention features a flexion joint apparatus, including a body including a proximal plate having a tongue and distal plate having a protrusion on either side of the distal plate and means for limiting the relative motion of the proximal plate with respect to the distal plate.

In another aspect, the invention features a method of installing an ankle joint in a leg brace, including pouring the cast, modifying the cast, mounting a dummy ankle joint having fixed range of motion, vacuum forming plastic on the cast, cooling the plastic and removing the brace.

One advantage of the invention is that the joint hinge tolerates misalignment and nonparallel mounting surfaces with respect to the leg brace, simplifying and speeding the fabrication and fitting process.

A further advantage of the invention is that the ankle joint assembly is compact in length and width and thin in the rotation axis dimension, generating minimal interference with the patient's shoes and allowing use with smaller patients, such as pediatric patients.

Another advantage of the invention is that the range of motion of the joint hinge and therefore a leg brace can be easily set by the patient or practitioner.

Another advantage of the invention is that a range limiting system allows the patient or practitioner to set a continuum of settings to meet the individual needs of a patient.

Another advantage of the invention is that the threaded rods in the range limiting system are set in the anterior and posterior directions.

Other advantages, features, and capabilities of the invention will become apparent from the following description taken in conjunction with the accompanying drawings showing the preferred embodiment of the invention.

BRIEF DESCRIPTION OF THE FIGURES

The present invention is described with reference to the accompanying drawings. In the drawings, like reference numbers indicate identical or functionally similar elements.

FIG. 7A illustrates a rear view of the embodiment of the leg brace of FIG. 6 showing a misalignment angle accommodated by the invention.

FIG. 7B illustrates a top view of the embodiment of the leg brace of FIG. 6 showing a misalignment angle accommodated by the invention.

FIG. 8 illustrates a cross section view of a fabrication model showing the conformal shaping of a leg brace.

FIG. 9 shows a molding dummy ankle joint for the fabrication model of FIG. 8.

DETAILED DESCRIPTION OF THE INVENTION

Figure 1A:
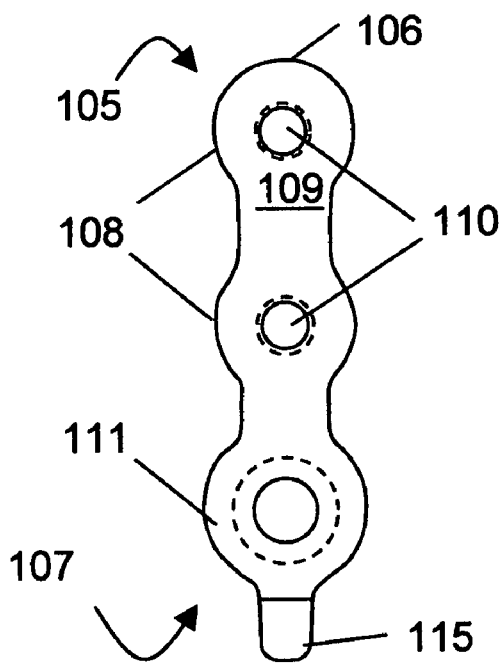
FIG. 1A-D illustrate respective front and side views of the constituent components of an embodiment of a flexion control ankle hinge apparatus.

The present invention pertains to an ankle joint providing rigid vertical support, allowing free ankle rotation within adjustable plantar and dorsiflexion limits while allowing angular misalignments that simplify fabrication and adjustment of a leg brace utilizing the ankle joint. The ankle joint results in a compact assembly easily adapted to smaller patients, including pediatric patients. These capabilities are achieved by an ankle joint comprising a proximal and distal plate joined by a spring loaded spherical dome hinge. The spherical dome is formed in one component, typically the distal plate, and a mating recess is formed in the other component, typically the proximal plate. The assembly is held together by a captive screw and spring wave washer. The distal plate further includes a rotation range limiting mechanism including dorsiflexion and plantar flexion limit adjustments. These features may be better understood with reference to the figures.

FIG. 1A-FIG. 1D illustrate respective front and side views of the constituent components of an embodiment of a flexion control ankle hinge apparatus 100. The apparatus 100 typically includes a proximal plate 105 and a distal plate 150. The distal plate 150 typically includes a dome feature 228 for coupling to the proximal plate 105. The proximal plate 105 typically includes a recess 224 for receiving the dome 228 of the distal plate 150. A captive screw 220 and wave washer 222 hold the dome 228 and surface of the recess 224 in contact and insure connection of the proximal 105 and distal 150 plates.

The proximal plate 105, which is comprised of an upper end 106 and lower end 107, typically includes one or more brace connection points 108 that are used in conjunction with a leg brace as described further below with respect to a flexion control ankle joint hinge system. One of the brace connection points 108 is typically located at the upper end 106 of the proximal plate 105. Another brace connection point 108 is typically positioned between the upper and lower ends 106, 107. The brace connection points 108 are typically wider than the overall width of the proximal plate 105 and may have a generally circular-shaped base 109. A hole 110 is also located approximately in the center of each base 109 of the connection points 108. The proximal plate 105 further includes a distal plate connection point 111 positioned adjacent the lower end 107. The distal plate connection point 111 includes a recess 224 formed to mate with the dome 228 of the distal plate. The recess 224 includes a through hole 226 to accommodate a shoulder screw 220 and wave washer 222 captive device.

The proximal plate 105 also includes a tongue 115 connected to the lower end 107 of the proximal plate 105. The tongue 115 is a protrusion and is generally narrower than the overall width of the proximal plate 105. In one embodiment, the tongue is slightly thicker than the remainder of the proximal plate. The tongue 115 is part of the overall range limiting system that is discussed further in the description below.

The proximal plate and tongue may include chamfering or contouring of the edges to allow greater range of motion in lateral directions.

Figure 1B:
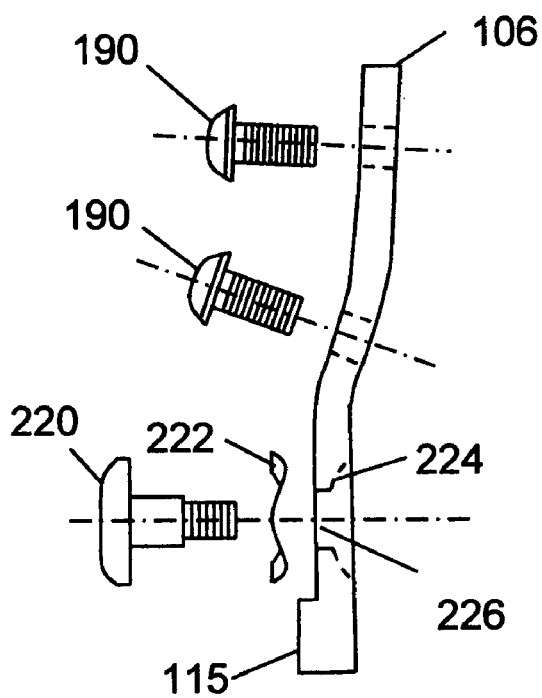
Figure 1C:
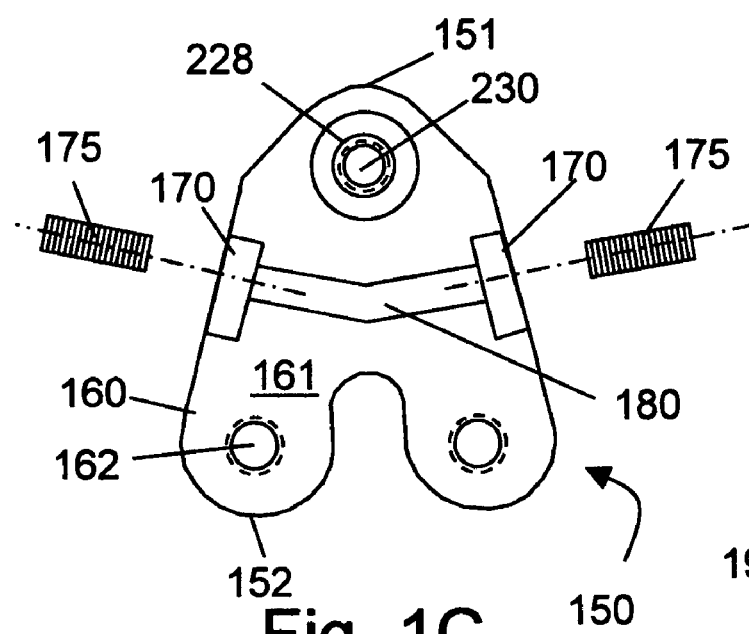

Referring to FIG. 1B and FIG. 1C, as shown in the side view of the proximal plate 105, the upper and lower ends 106, 107 of the proximal plate 105 are offset from each other due to a gradual curvature of the proximal plate 105. A portion of the lower end 107 is elevated slightly with respect to the upper end 106. A bend, causing the overall curvature, in the proximal plate 105 typically achieves this elevation differential. As described further below, when the distal plate 150 and proximal plate 105 are connected, this elevation differential results in the upper end 106 of the proximal plate 105 and the distal plate 150 being oriented in a similar positional plane.

Figure 1D:
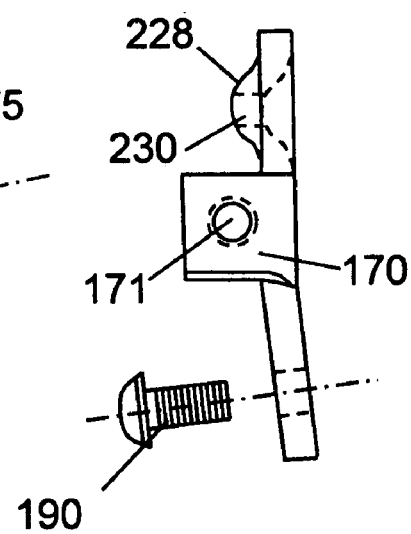

The distal plate 150 generally includes an upper end 151 and a lower end 152. The upper end 151 of the distal plate 150 includes a proximal plate connection point 155. The proximal plate connection point 155 generally includes a smooth outer curvature 158 that generally follows the resulting path of curvature of the proximal plate 105 with respect to the distal plate 150 when the two are attached and move with respect to one another. The proximal plate connection point 155 generally includes a dome feature 228 raised from the surface of the distal plate 150 in the direction of the proximal plate 105. The dome feature 228 includes a threaded hole 230 through the top of the dome for receiving the captive screw 220. The dome 228 may be fabricated as in at least two embodiments, a formed embodiment as shown in FIG. 1D and a separate component as described later below with reference to FIG. 5A.

The lower end 152 of the distal plate 150 typically includes two brace connection points 160. Similar to the brace connection points 108 of the proximal plate 105, the brace connection points 160 of the distal plate 150 have a generally circular-shaped base 161. A hole 162 is also located approximately in the center of each base 161 of each brace connection point 160.

The distal plate 150 further includes a tongue-stop 170 on each side of the distal plate 150, located generally between the upper and lower ends 151, 152. The tongue-stops 170 are typically a small plate protrusion generally perpendicular to the overall surface of the distal plate 150, although other angles are anticipated. Each of the tongue-stops 170 includes threaded holes 171 through which the threaded rod 175 is typically connected in threaded engagement. The threaded rods may include nylon or similar inserts to maintain friction contact to prevent movement of the adjustment once the proper setting is established. Alternatively, a thread locking compound may be used to set the thread position. The tongue-stops 170 are part of the overall range limiting system that is discussed further in the description below. A conduit 180, if provided, may be located on a portion of the distal plate 150 adjacent the tongue-stops 175. The conduit 180 is generally oriented to receive the threaded rods 175 as the rods 175 transverse through the holes 171 on the tongue stops 170 as they are screwed into and out of the tongue stops 170. Since the threaded rods 175 are not typically oriented in opposition, the conduit 180 typically bends, thereby generally changing the direction of the conduit 180, at an approximate center location of the distal plate 150. In other embodiments, the threaded rods 175 can be oriented in opposition and, therefore, the conduit 180 can be in a continuous straight line.

As shown in the side view of the distal plate 150, the upper and lower ends 151, 152 of the distal plate 150 are offset from each other due to a gradual curvature of the distal plate 150. A portion of the lower end 152 is curved slightly with respect to the upper end 151. As described further below, when the distal plate 150 and proximal plate 105 are connected, this elevation differential results in the upper end 106 of the proximal plate 105 and the lower end 152 of the distal plate 150 being oriented in a similar positional plane.

The apparatus 100 further includes several screws 190 that can be used to connect the apparatus 100 to a leg brace to form an overall brace system. In general, the screws 190 can be used to engage the holes 110, 162 in the brace connection points 111, 160 of the proximal and distal plates 105, 150 respectively. The holes 110, 162 can include threads so that the screws 190 can be in threaded engagement with the screws 190. The apparatus 100 can further include an external adjustment instrument, such as a hex wrench which can be used to adjust the threaded rods 175 within the holes 171 of the tongue-stops 170 as part of the overall range limiting system. The apparatus 100, the screws 190 and the adjustment instrument can be included together as an overall leg brace kit.

Figure 2:
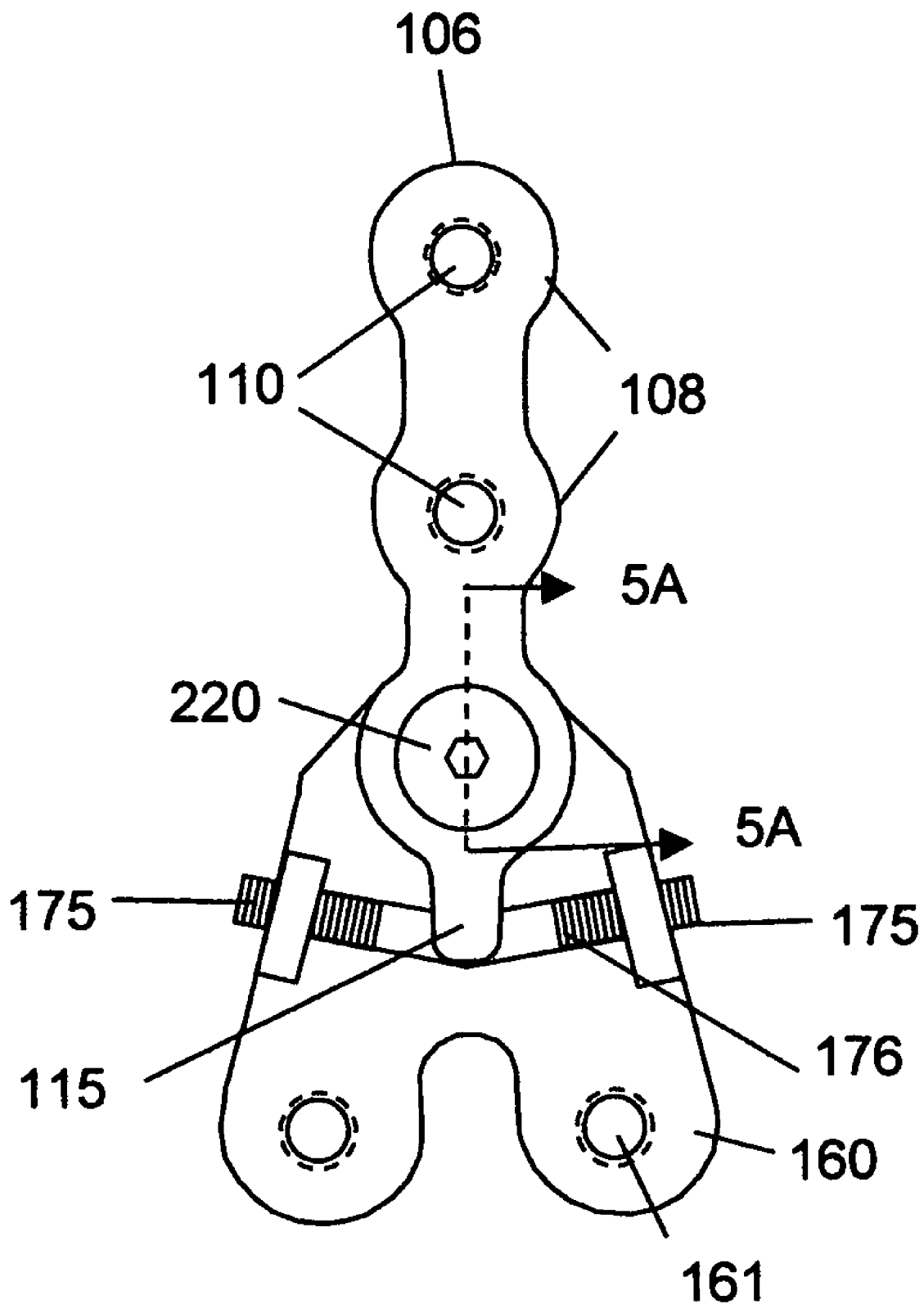
FIG. 2 illustrates a front view of an embodiment of a flexion control ankle joint hinge assembly using the components of FIG. 1A-FIG. 1D.

FIG. 2 illustrates a front view of an embodiment of a flexion control ankle joint hinge apparatus 100. The apparatus 100 generally includes the proximal plate 105 and a distal plate 150 that are pivotally connected to each other. The connected proximal and distal plates 105, 150 make up a main body in which the proximal and distal plates 105, 150 pivot with respect to each other. The front view shows the connection point connecting the proximal and distal plates allowing rotation while accommodating misalignments. Also shown is the rotation limit tongue and adjustment screws.

With the component pieces assembled in this manner, the distal and proximal plates 105, 150 remain connected to each other. The plates 105, 150 can pivot with respect to each other about an axis generally aligned with the captive screw 220 and the plates may rotate by traversing along the surface of the dome along axes generally perpendicular to the captive screw. The captive screw 220 and spring wave washer 222 maintain contact between the proximal 105 and distal 150 plates and prevents the component pieces from coming disassembled.

The range limiting system is mentioned shortly in the above description with respect to the tongue 115 and the tongue-stops 170. The range limiting system is now described with respect to the assembled flexion control ankle joint hinge apparatus 100. In the assembled state, the tongue 115 generally pivots above the surface of the distal plate 150 as the proximal plate 105 is rotated with respect to the distal plate 150. The range of movement of the tongue 150 generally follows the path of the conduit 180 on the distal plate 150. By following the general path of the conduit 180, the tongue 115 is limited in its outward motion by coming into contact with the tips 176 of the threaded rods 175 as they sit in a portion of the conduit 180 when in threaded engagement with the tongue-stops 170. With the threaded rods 175 removed or screwed outward to a point so that the tips of the rods 175 do not protrude from the inner portion of the tongue-stop protrusions 170, the tongue 115 generally moves in its widest range of motion. The outer motion of the tongue 115 is limited when its contacts the tongue stops 170. In this orientation, the maximum outward motion of the apparatus 100 is defined. In an opposite extreme, the threaded rods 175 can be screwed inward to their maximum inward position, in which the tips 176 of both the threaded rods 175 contact the tongue 115 at the same time, thereby allowing no motion of the tongue 115 to occur. The threaded rods 175 can be adjusted slightly to still keep the tongue 115 and therefore the proximal plate 105 from rotating with respect to the distal plate 150 and to allow the proximal plate 105 to be oriented in a fixed position with respect to the distal plate 150. As shown in the figures, the threaded rods 175 are oriented in the anterior and posterior directions. By being oriented in the anterior and posterior directions, the apparatus 100 can be adjusted easily without having to remove the brace as described further below. In a typical implementation, the threaded rods 175 can be adjusted with an Allen (or hex) wrench. A typical Allen wrench includes a ninety degree angle so that when a user reaches down the forward portion of the Allen wrench is naturally positioned in the posterior and anterior direction. It is further appreciated that each of the threaded rods 175 can be adjusted and optionally fixed so that the proximal plate 105 moves in a fixed direction or is positioned in a fixed angular position with respect to the distal plate 150.

As described further below with respect to the flexion control ankle joint hinge apparatus 100 connected to a leg brace, it is typically desired to allow some range of motion depending on the level of therapy of the patient wearing the brace. Therefore, the threaded rods 175 are typically threaded to a setting that allows the tongue 115 to move with some limited motion, thereby allowing the proximal and distal plates 105, 150 to pivot with respect to each other. As can be appreciated by the above description in conjunction with the figures, there is a continuum of positions that are possible by setting the threaded rods 175. It is further appreciated that this range limiting system allows a patient and practitioner to fine tune settings of the apparatus to meet the many different needs of different patients.

Figure 3:
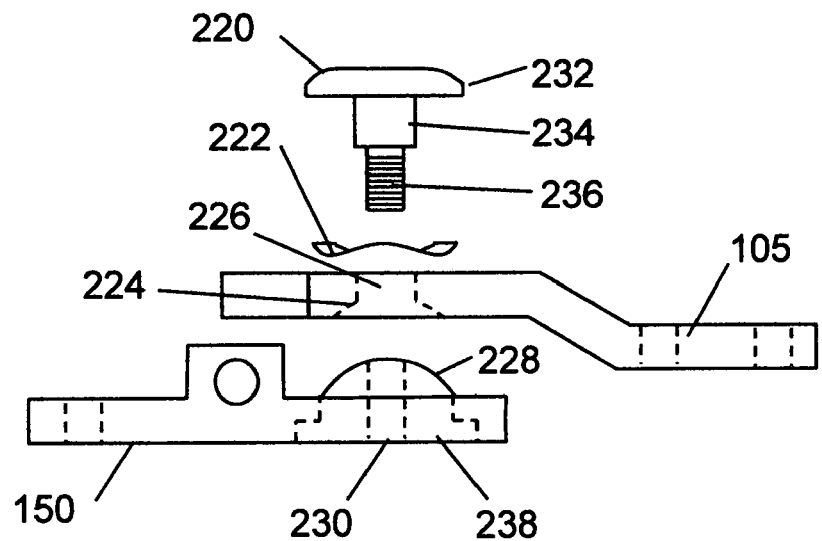
FIG. 3 illustrates an exploded side view of the assembly of FIG. 2.

FIG. 3 illustrates an exploded side view of the assembly of FIG. 2. FIG. 3 also illustrates the dome being formed by a separate component. FIG. 3 shows the distal plate, with the dome, the proximal plate with the recess for receiving the dome and the through hole. The shoulder screw 220 is shown aligned with the through hole 226 in the proximal plate and the threaded hole 230 through the top of the dome 228. The spring wave washer 222 is shown positioned between the head 232 of the shoulder screw 220 and the surface of the proximal plate 105.

Figure 4A:
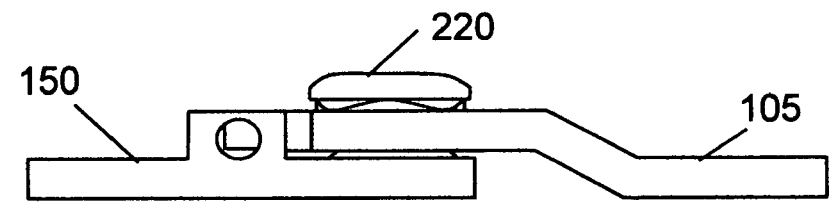
FIG. 4A-FIG. 4C illustrate the assembled side view and illustrate different bends for the ends of the embodiment of FIG. 3.
Figure 4B:
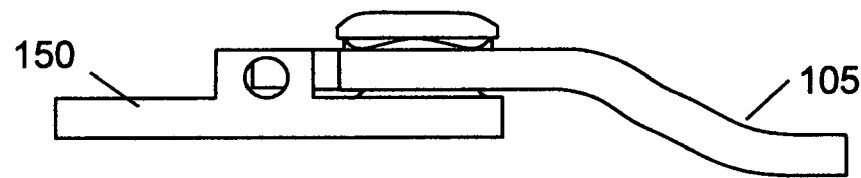
Figure 4C:
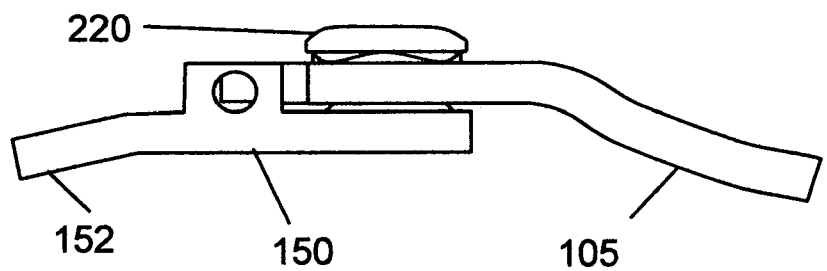

FIG. 4A-FIG. 4C illustrate the assembled side view and illustrate different bends for the ends of the embodiment of FIG. 3. The side view of FIG. 4A illustrates the relative position of the proximal and distal plates 105, 150 with respect to each other showing certain dimensional features. Specifically, as mentioned above, there is an elevation differential between the upper and lower ends 106, 107 of the proximal plate 105. When the proximal and distal plates 105, 150 are assembled, the upper end 106 of the proximal plate 105 is generally in the same plane as the lower end 152 the distal plate 150 and the lower end 107 of the proximal plate 105 is located in a plane generally parallel to overall orientation of the distal plate 150.

FIG. 4B and FIG. 4C illustrate additional embodiments wherein the proximal plate 105 is further curved and wherein the lower end 152 of the distal plate 150 is slightly curved. These features allow accommodation of different leg brace interface surfaces.

Figure 5A:
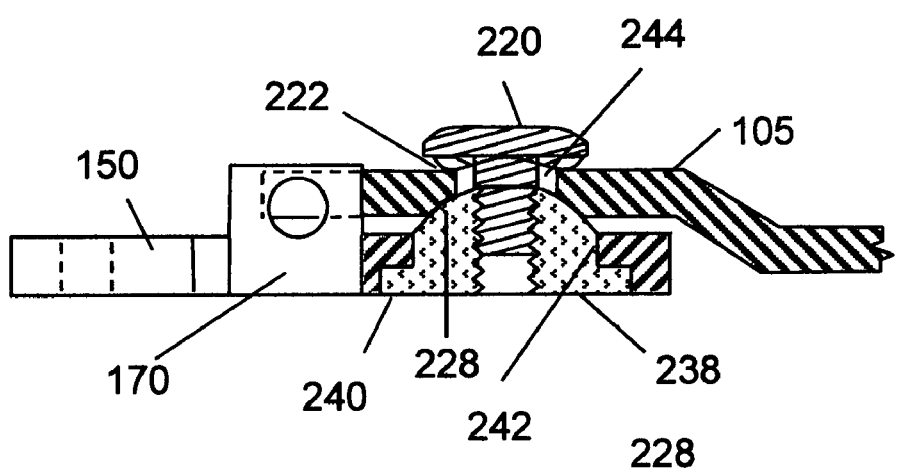
FIG. 5A illustrates a separate component forming the dome of the cylindrical connection.

FIG. 5A illustrates the use of a separate component to form the dome of the cylindrical connection. FIG. 5A illustrates the proximal plate 105 and distal plate 150 in a partial cross section side view. The cross section cut is identified in FIG. 2. Referring to FIG. 5A, the distal plate 150 includes the dome component 238 inserted and attached to the distal plate 150. The dome component 238 is formed with a wide cylindrical base 240, a slightly narrower cylindrical midsection 242 followed by the dome portion 228 on top. The dome component 238 has a threaded hole 228 in the center to receive the threaded portion 234 of the captive screw 220. The proximal plate 105 rests on top of the dome 228 with the surface of the matching recess 224 in contact with the spherical dome 228. The shoulder screw 220 holds the spring wave washer 222 in place to apply a preload pressure to the proximal plate 105 in contact with the dome 228. A space 244 is provided between the shoulder 234 of the captive screw 220 and the proximal plate 105 to allow movement of the proximal plate 105. The proximal plate 105 does not normally press against the captive screw 220 unless the proximal plate exceeds the mechanical limits of rotation along the surface of the dome 228 or unless disruptive forces exceed the preload of the spring wave washer 222, in which case, the captive screw 220 serves to maintain connection integrity of the ankle joint 100.

In one embodiment, the dome component 238 is fabricated from a bearing type material, for example, sintered bronze. Sintered bronze may be impregnated with a lubricant. Other bearing type materials may be substituted. The dome component may be affixed by press fitting, brazing, welding, swaging, threading, adhesive, or other means appropriate to the material. As shown, the dome component 238 has a threaded through hole. In an alternative, the hole may be closed at the bottom end (not shown).

The distal and proximal plates and dome component may be medical grade stainless steel, or titanium, although other materials including composites and certain high strength plastics may also be used.

Figure 5B:
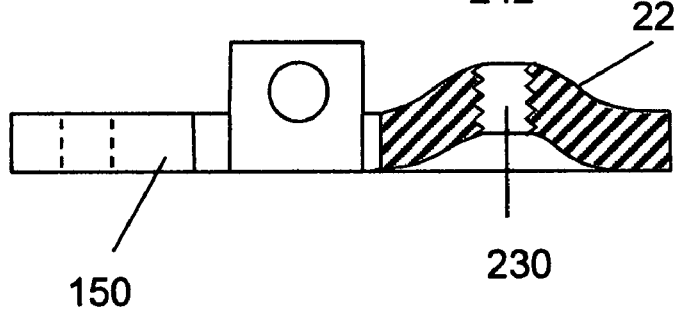
FIG. 5B illustrates a formed embodiment for the dome of the cylindrical connection.

FIG. 5B illustrates a formed embodiment for the dome 228 of the cylindrical connection. FIG. 5B shows the distal plate 150 portion of FIG. 5A using the cut section shown in FIG. 2. Referring to FIG. 5B, the dome portion 228 is formed from the distal plate material by press forming, forging, casting, milling, or other methods. The threaded hole 230 is provided for the captive screw 220.

More generally stated and applicable generally to FIG. 5A or 5B, the captive screw may be a captive stud or pin having a shank portion passing through the through hole in the mating cavity surface, the captive pin having an enlarged cap portion 232 incapable of passing through the through hole in the mating cavity surface. The captive pin may be affixed by other means than by threading, such as by press fitting, swaging, brazing, welding, gluing or other means known in the art for affixing studs. Alternatively, the cap portion 232 may screw onto or otherwise be attached to the stud 234 for holding the wave washer.

Figure 6:
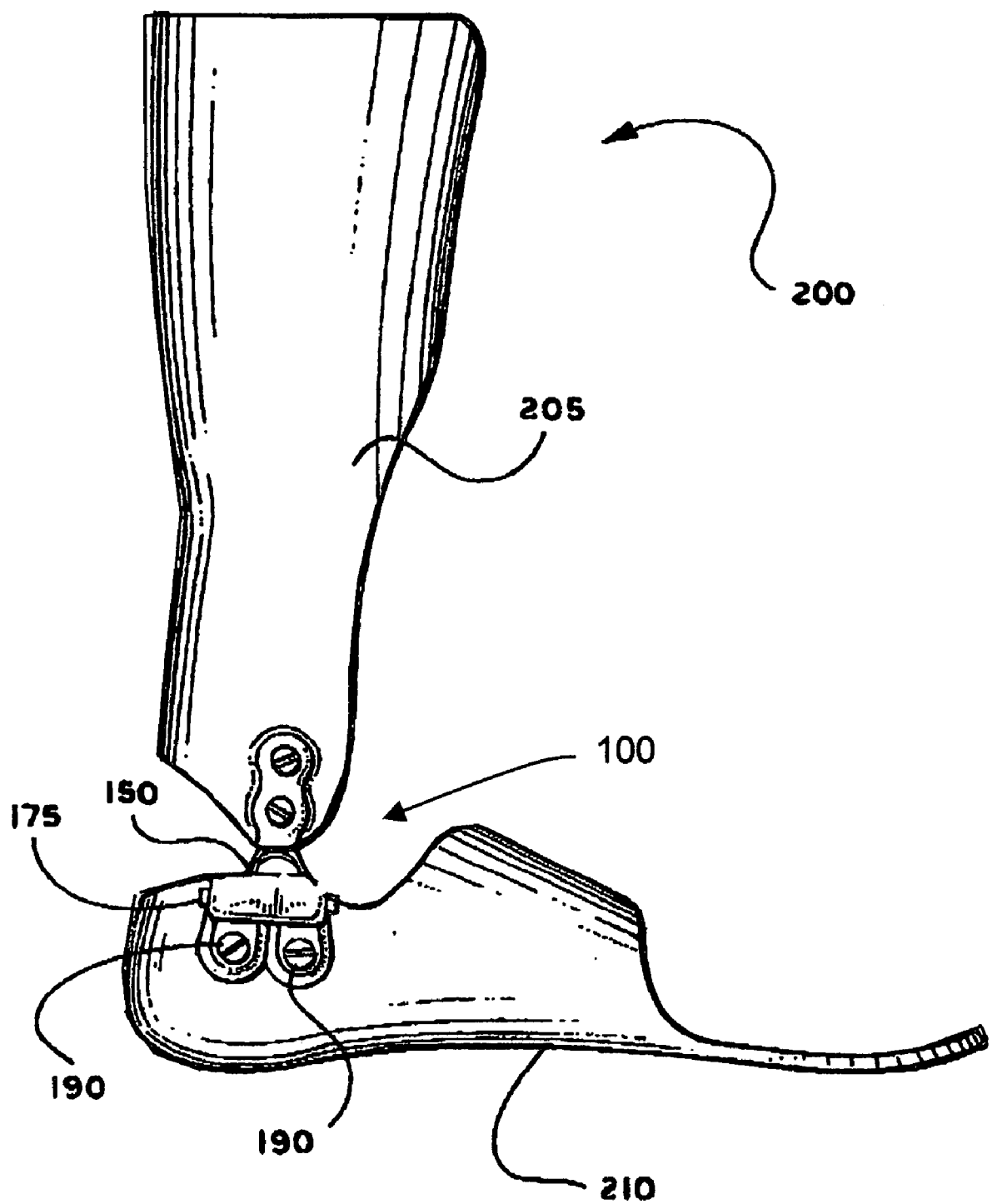
FIG. 6 illustrates an embodiment of a leg brace having an embodiment of flexion control ankle joint hinge apparatus connected to the brace.

FIG. 6 illustrates an embodiment of a leg brace 200 having an embodiment of flexion control ankle joint hinge apparatus 100 connected to the brace 200. The brace 200 is generally manufactured with dies that are pre-contoured to a particular patient. In another embodiment, the brace 200 can be prefabricated. In general, the brace 200 includes the apparatus 100 as described above. Typically, the brace 200 includes an upper or proximal portion 205 and a lower or distal portion 210. The proximal plate 105 is fixed to the proximal portion 205 of the brace 200 through the brace connection points 108 and screws 190 as described above. The distal plate 150 is fixed to the distal portion 210 of the brace 200 through the brace connection points 160 and screws 190 as also described above. In another implementation, if the patient requires that their ankle remained pointed in one direction, dorsal or plantar, then only one threaded rod can be used, either on the posterior or anterior side.

As described above, the anterior-posterior adjustment of the system provides several advantages. If a practitioner is observing, for example, the gait of a patient wearing the brace 200, the practitioner can make easy adjustments by setting the threaded rods 175 without the patient having to doff the brace 200. Either the practitioner or the patient can easily adjust the level of control, say the dorsal and plantar flexion. As is further appreciated in the description below, the brace 200 can be custom contoured to the patient then fitted with the apparatus 100 to allow a custom fit for each individual patient.

Furthermore, some patients require free plantar flexion, that is, the ankle can be bent so that the foot points downward, yet no dorsiflexion, that is, bending the ankle so that the foot points upward. The range limiting system as described above allows this type of setting to be attained by the patient. The range limiting system allows the degree of plantar flexion to be easily set. In addition, the ankle joints can be reversed so that there is free dorsiflexion.

FIG. 7A illustrates a rear view of the embodiment of the leg brace of FIG. 6 showing a misalignment angle accommodated by the invention. Referring to FIG. 7A, the proximal portion of the leg brace 205 is connected to the distal portion 210 using two spherical dome ankle hinges 100 in accordance with the present invention. Typical fabrication processes may leave imprecise mounting surfaces or out of square alignments to be accommodated by the practitioner, either by modification or by re-fabrication; however, these errors may be accommodated by the spherical dome hinge 100, saving the time and effort of modification or refabrication. FIG. 7A shows a gravity line axis 270 and a square lateral axis 272. Ideally the hinges should line up along the square lateral axis 272; however the hinges shown are off by axis 274. The mounting surfaces should also line up (perpendicular) to the square lateral axis and should be parallel to one another. However, as shown, the proximal portion 205 has a mounting surface angle 250 and the associated distal portion 210 has a mounting surface angle 252. The difference angle 254 may otherwise cause rubbing and wear issues in a prior art hinge and stress flexing and cracking issues in the leg brace parts; however, the spherical dome hinge accommodates this angle by allowing the proximal plate to find the correct location on the mating surface of the dome.

FIG. 7B illustrates a top view of the embodiment of the leg brace of FIG. 6 showing a misalignment angle accommodated by the invention. In a similar manner to the mounting surface misalignments of FIG. 7A, the mounting surfaces of FIG. 7B may be misaligned as viewed from above. FIG. 7B shows the perpendicular axis 272 and a forward axis 278 along the foot. The ankle joints may be offset from the perpendicular axis 272 along axis 276. Also, the top may be at angle 260, the bottom at angle 262, generating a difference angle 264. Again, the spherical dome hinge 100 accommodates this angle by allowing the proximal plate to find the correct location on the mating surface of the dome.

FIG. 8 illustrates a cross section view of a fabrication model showing the conformal shaping of a leg brace. First, a comparison is made relative to a prior design ankle joint as described in U.S. Pat. No. 6,929,614 incorporated by reference above. A typical prior metal ankle joint is squared before plastic is added. If squaring is not precise, the misalignment can cause premature wearing. If the ankle joint is not square the ankle joints wear out in the medial and lateral directions, that is, the brace may widen or narrow at the level of the ankle. In a typical implementation, the ankle axis is first located on a negative cast. The cast is drilled at this location and a squaring rod is inserted. The hole is sealed so that there is no subsequent leakage. Then the cast is poured. After the cast has set, then the squaring rod is removed. The resultant cast is a positive cast of the patient's leg with a hole through the ankle axis. The cast is then modified, that is, it is built up in the ankle. A rod that is used to hold square with the ankle is inserted through the hole. At this point, plastic is vacuum formed. Once the plastic has cooled, it is removed from the cast. The plastic is cut all around and the brace is removed. Since the squaring rod is in the way, the hole is cut. The brace is generally removed easily at this point.

Without the spherical hinge, the steps are:
1) making a shell casting of the leg;
   a) adding a pilot squaring rod at the ankle hinge point;
2) making a plaster copy of the leg using the shell casting, including the squaring rod;
   a) removing the pilot squaring rod;
   b) inserting hinge holder in hole vacated by squaring rod in plaster;
3) building up a joint mount on the plaster cast;
   a) mounting hinge on hinge holder;
4) mounting the hinge holder and ankle joint on the built up part of plaster
5) wrapping and forming softened plastic around the leg copy and ankle joint;
6) cooling and remove plastic; and
7) trimming plastic and mounting ankle joint on plastic.

In accordance with the invention, a leg brace may be fabricated by:
1) making a shell casting of the leg;
2) making a plaster copy of the leg using the shell casting;
3) building up a joint mount on the plaster cast;
4) mounting a molding dummy ankle joint on the built up part of plaster;
5) wrapping and forming softened plastic around the leg copy and ankle joint;
6) cooling and remove plastic; and
7) trimming plastic and mounting ankle joint on plastic.

Thus, steps 1a, 2a, 2b, and 3a pertaining to the squaring rod and mounting devices are eliminated. Thus, the hinge of the present invention may save a significant amount of time in the fabrication of a leg brace, resulting in a potentially lower cost product. The elimination of misalignment problems further improves life of the leg brace. Details of the new process may better be understood with reference to FIG. 8.

FIG. 8 is a top view cross section through the plane of the ankle joint hinge. Shown are the plaster casting 280 of the leg, a plaster build up 284 for the ankle joint, a molding dummy 290 in place of the ankle joint, and the leg brace plastic 282. The objective of the assembly is to wrap heated and softened leg brace plastic sheet 282 around the fabrication model and vacuum form the plastic to the shape of the fabrication model. The plastic is typically polypropylene, although other plastics may be used. The plaster casting 280 of the leg is made by fabricating a shell casting around the leg, which is cut, removed from the leg, reassembled, and filled with plaster. The plaster build up 284 is added to insure separation of the ankle joint from the leg so that the ankle joint will not rub on the leg. A molding dummy ankle joint 290 is used in place of an actual ankle joint 100 during fabrication to insure that the plastic is set with the ankle joint in a predetermined (centered) position, since the ankle joint may flex in any direction under the stresses encountered during vacuum forming of the plastic. The molding dummy may be essentially an ankle joint which is fixed in the proper orientation, i.e., centered in the plane of the ankle joint and adjusted for proper bias, if any. A molding dummy may be made as a single unit resembling an ankle joint in outer dimension, but held in fixed position, not able to twist or rotate. The molding dummy may be made from any suitable material including plastics and may be molded from low cost plastic. In one embodiment, the molding dummy may be a single piece molded part. Alternatively, a molding dummy may be made by modifying an ankle joint as shown in FIG. 9.

FIG. 9 shows a molding dummy ankle joint for the fabrication model of FIG. 8. FIG. 9 shows the proximal 105 and distal 150 plates. The wave washer 222 is replaced with a solid washer 292 allowing the shoulder screw 220 to tighten against the proximal plate 105, holding the proximal plate 105 parallel to the distal plate 150. Alternatively, a different screw (shorter) 220 may be used to hold the proximal plate 105 directly without the need for a washer 292 to fill the space of the wave washer 222. The molding dummy 290 may be adjusted for any plantar flexion or dorsiflection angle desired by adjusting the threaded rods 175, although the typical adjustment would be for straight alignment, i.e. the alignment of FIG. 2 would be set by adjusting the threaded rods 175 for the centered position shown, but without any range of motion.

The molding dummy may then be attached by screws or other methods to the built up portion of the plaster fabrication model. The plastic sheet is then heated and wrapped, vacuum formed and allowed to cool. The cooled plastic is then trimmed to shape and removed from the plaster. Holes may be drilled in the plastic for the hinge by placing the hinge in the recess formed by the molding dummy and using the hinge holes to guide the drill. Screws may then be inserted to mount the ankle joint.

Thus, the leg brace may be fabricated without installation of a squaring rod and without undue attention with the squaring process because of the ankle joint's tolerance of misalignments. Since the squaring process is a time consuming part of prior fabrication, the new ankle joint results in saving of significant time and effort. Further, the leg brace is expected to wear better and longer, especially compared to prior type units that are marginally or poorly squared during the manual fabrication process.

Variations

Although the ankle joint is shown with the dome on the distal plate and mating depression on the proximal plate, the dome and depression may be reversed, with the dome on the proximal plate and mating depression on the distal plate. As a further variation, the dome may face inward, toward the ankle or outward, as shown in the figures. As a further variation, the leg brace may be configured in reverse, with the proximal plate to the lower side and the distal plate to the upper side. The components may be fabricated of any suitable material including stainless steel, steel, titanium, aluminum, brass, bronze, plastic, re-enforced plastic or any other suitable material or combination of materials. Accordingly, component fabrication may be by stamping, casting, forging, molding or other techniques appropriate for the material.

One should understand that numerous variations may be made by one skilled in the art based on the teachings herein. While various embodiments of the present invention have been described above, it should be understood that they have been presented by way of example only, and not limitation. Thus, the breadth and scope of the present invention should not be limited by any of the above-described exemplary embodiments, but should be defined only in accordance with the following claims and their equivalents.

What is claimed is:

1. A flexion control ankle joint apparatus, comprising:
   1) a proximal plate having an upper end and a lower end;
   2) a distal plate coupled to the proximal plate through a spherical dome coupling, said spherical dome coupling comprising:
      a) a spherical dome;
      b) a mating cavity surface, said mating cavity surface in contact with said spherical dome, said mating cavity surface having a through hole; said spherical dome presenting a spherical surface for contacting said mating cavity surface, said spherical surface consisting of a portion of a hemisphere less than a full hemisphere;
      c) a captive pin attached to said spherical dome, said captive pin having a shank portion passing through said through hole in said mating cavity surface, said captive pin having an enlarged portion incapable of passing through said through hole in said mating cavity surface; and
      d) a spring for providing a preload force to hold said spherical dome and said proximal plate in contact; and
   3) a range limiting system, comprising:
      a) a tongue connected to the lower end of the proximal plate;
      b) two tongue-stops connected to the distal plate at a generally perpendicular orientation,
   wherein each of the tongue-stops includes a threaded hole through which a threaded rod is connected to the tongue-stops in threaded engagement.

2. The flexion control ankle joint apparatus of claim 1, wherein the dome comprises a dome component fabricated separately from the distal plate and attached to the distal plate.

3. The flexion control ankle joint apparatus of claim 2, wherein the dome component comprises sintered bearing material.

4. The flexion control ankle joint apparatus of claim 2, wherein the dome component is affixed by pressing, threading, welding, brazing, swaging or gluing.

5. The flexion control ankle joint apparatus of claim 1, wherein the dome is attached to the distal plate and the mating cavity surface is in the proximal plate.

6. The flexion control ankle joint apparatus of claim 1, wherein the dome is attached to the proximal plate and the mating cavity surface is in the distal plate.

7. The flexion control ankle joint apparatus of claim 1, wherein the dome is formed from the same material as the distal plate.

8. The flexion control ankle joint apparatus of claim 1, wherein the spring comprises a spring wave washer.

9. The flexion control ankle joint apparatus of claim 1, wherein the captive pin comprises a shoulder screw.

10. The flexion control ankle joint apparatus of claim 1, wherein the captive pin is affixed by threading, pressing, swaging, welding, brazing, or gluing.

11. The flexion control ankle joint apparatus as claimed in claim 1, further comprising a conduit located on the distal plate and partially surrounding each of the threaded rods.

12. A leg brace system, comprising:
   a leg brace comprising a proximal portion having a first mounting surface and a distal portion having a second mounting surface; and
   at least one flexion joint apparatus as in claim 1 mounted on said first mounting surface and said second mounting surface, thereby allowing slight angular misalignment between said first mounting surface and said second mounting surface.

* * * * *